United States Patent
Langdon et al.

[11] Patent Number: 5,693,169
[45] Date of Patent: Dec. 2, 1997

[54] METHOD FOR MAKING A CAPILLARY LAMINATE MATERIAL

[75] Inventors: Frederick M. Langdon, Kobe, Japan; John B. Burchnall, West Chester, Ohio; Gregory B. Hyde, Covington, Ky.

[73] Assignee: The Procter & Gamble Company, Cincinnati, Ohio

[21] Appl. No.: 518,149

[22] Filed: Sep. 7, 1995

[51] Int. Cl.⁶ ................................................ B32B 03/10
[52] U.S. Cl. .................. 156/252; 156/263; 156/285; 156/291
[58] Field of Search ........................ 156/290, 182, 156/251, 252, 253, 256, 263, 277, 285, 324, 291; 427/131, 137

[56] References Cited

U.S. PATENT DOCUMENTS

| | | | |
|---|---|---|---|
| 3,628,720 | 12/1971 | Schmedding | 229/55 |
| 3,945,386 | 3/1976 | Anczurowski et al. | 128/287 |
| 4,064,300 | 12/1977 | Bhangu | 428/120 |
| 4,276,338 | 6/1981 | Ludwa et al. | 428/137 |
| 4,338,366 | 7/1982 | Evans et al. | 428/76 |
| 4,414,255 | 11/1983 | Tokuyama et al. | 428/154 |
| 4,438,167 | 3/1984 | Schwarz | 428/138 |
| 4,450,195 | 5/1984 | Hagbjer | 428/178 |
| 4,587,152 | 5/1986 | Gleichenhagen et al. | 428/195 |
| 4,609,518 | 9/1986 | Curro et al. | 264/504 |
| 4,629,643 | 12/1986 | Curro et al. | 428/131 |
| 4,636,424 | 1/1987 | Amemuya et al. | 428/198 |
| 4,723,953 | 2/1988 | Rosenbaum et al. | 604/369 |
| 4,808,675 | 2/1989 | Twilley et al. | 525/408 |
| 4,839,216 | 6/1989 | Curro et al. | 428/134 |
| 4,847,142 | 7/1989 | Twilley et al. | 428/252 |
| 4,898,761 | 2/1990 | Dunaway et al. | 428/137 |
| 4,948,653 | 8/1990 | Dinter et al. | 428/172 |
| 5,028,332 | 7/1991 | Ohnishi | 210/500.34 |
| 5,116,661 | 5/1992 | Matsubara | 428/198 |
| 5,154,960 | 10/1992 | Mucci et al. | 428/68 |
| 5,261,899 | 11/1993 | Visscher et al. | 604/367 |
| 5,368,909 | 11/1994 | Langdon et al. | 428/137 |
| 5,500,270 | 3/1996 | Langdon et al. | 428/119 |
| 5,599,606 | 2/1997 | Disselbeck et al. | 428/156 |

FOREIGN PATENT DOCUMENTS

| | | | |
|---|---|---|---|
| 0496567 | 7/1992 | European Pat. Off. | A61F 13/15 |
| 0 545 423 A1 | 6/1993 | European Pat. Off. | A61F 13/15 |

*Primary Examiner*—Michael W. Ball
*Assistant Examiner*—Michael A. Tolin
*Attorney, Agent, or Firm*—William Scott Andes; E. Kelly Linman; Jacobus C. Rasser

[57] ABSTRACT

The present invention relates to a method for making laminate materials, and more particularly the present invention relates to a method for making laminate materials having a capillary zone or passageway to acquire, move and/or store fluid within the laminate material. Such laminate materials are particularly suitable for use as a topsheet, an acquisition layer and/or an absorbent core in absorbent articles such as disposable diapers, catamenials, sanitary napkins, bandages, incontinent briefs and the like.

20 Claims, 5 Drawing Sheets

METHOD FOR MAKING A CAPILLARY LAMINATE MATERIAL

TECHNICAL FIELD

The present invention relates to a method for making laminate materials, and more particularly the present invention relates to a method for making laminate materials having a capillary zone or passageway to acquire, move and/or store fluid within the laminate material. Such laminate materials are particularly suitable for use as a topsheet, an acquisition layer and/or an absorbent core in absorbent articles such as disposable diapers, catamenials, sanitary napkins, bandages, incontinent briefs and the like.

BACKGROUND OF THE INVENTION

It has long been known in the disposable absorbent article art that it is extremely desirable to construct absorptive devices such as disposable diapers, catamenials, sanitary napkins, bandages, incontinent briefs, and the like, presenting a dry surface feel to the user to improve wearing comfort and to minimize the development of undesirable skin conditions due to prolonged exposure to moisture absorbed within the article.

Recently, capillary laminate materials comprised of at least two layers or sheets having a capillary zone between the sheets have been developed to address this previously unmet consumer need. The capillary zone between the sheets is established and maintained by at least one spacer element which simultaneously holds the two layers apart and keeps them from separating further. In a preferred embodiment the capillary laminate material includes a plurality of spacer elements. At least one of the sheets is fluid pervious to allow entry of fluid into the capillary zone. All layers may be rendered fluid-pervious, and such materials may include more than two layers as well. Capillary laminate materials of this variety are described in greater detail in commonly-assigned U.S. patent applications Ser. Nos. 08/212,487, filed Mar. 14, 1994 in the names of Langdon, et al., and 08/442,717, filed May 15, 1995 in the names of Langdon, et al., the disclosures of which are hereby incorporated herein by reference.

SUMMARY OF THE INVENTION

The present invention provides a process for forming a three-dimensional, macroscopically-expanded capillary laminate web comprised of a first sheet of polymeric material and a second sheet of polymeric material. The first sheet is fluid pervious, and the first sheet and the second sheet are spaced apart from one another by a plurality of spacers to define a capillary zone therebetween for the capillary movement of fluid. The first and second sheets are fed onto a first forming structure having opposed surfaces such that the second sheet is in contact with the first forming structure and the first sheet is in contact with the second sheet. At least one of the sheets, preferably the second sheet, has a plurality of spacers on the side facing the other sheet. The first forming structure exhibits a multiplicity of apertures which place the opposed surfaces of the first forming structure in fluid communication with one another. A fluid pressure differential is applied across the thickness of the first and second sheets which is sufficiently great as to cause the first and second sheets to rupture in those areas coinciding with the apertures in the first forming structure and to conform with the first forming structure.

In a preferred embodiment of the process of the present invention, the first sheet is rendered fluid pervious prior to feeding the first sheet onto the second sheet by feeding the first sheet onto a second forming structure. The second forming structure exhibits a multiplicity of apertures which place the opposed surfaces of the second forming structure in fluid communication with one another. A fluid pressure differential is applied across the thickness of the second sheet which is sufficiently great as to cause the second sheet to rupture in those areas coinciding with the apertures in the second forming structure and to conform with the second forming structure.

In another preferred embodiment of the process of the present invention, a second fluid pressure differential is applied to the second sheet after the second sheet is fed onto the forming structure but before the first sheet is fed onto the second sheet.

In still another preferred embodiment of the process of the present invention, the first and second sheets are pre-wound together onto a supply roll with the spacer elements therebetween, and simultaneously fed onto the forming structure.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify like elements throughout the drawings, and wherein:

DETAILED DESCRIPTION OF THE INVENTION

While the present invention will be described in the context of producing capillary laminate materials particularly suited for use in disposable absorbent articles, more particularly in the context of sanitary napkins, the present invention is in no way limited to such applications. To the contrary, the present invention may be practiced to great advantage whenever it is desired to produce capillary laminate materials not previously obtainable using prior art web forming processes.

Capillary Laminate Materials.

Figure 1:
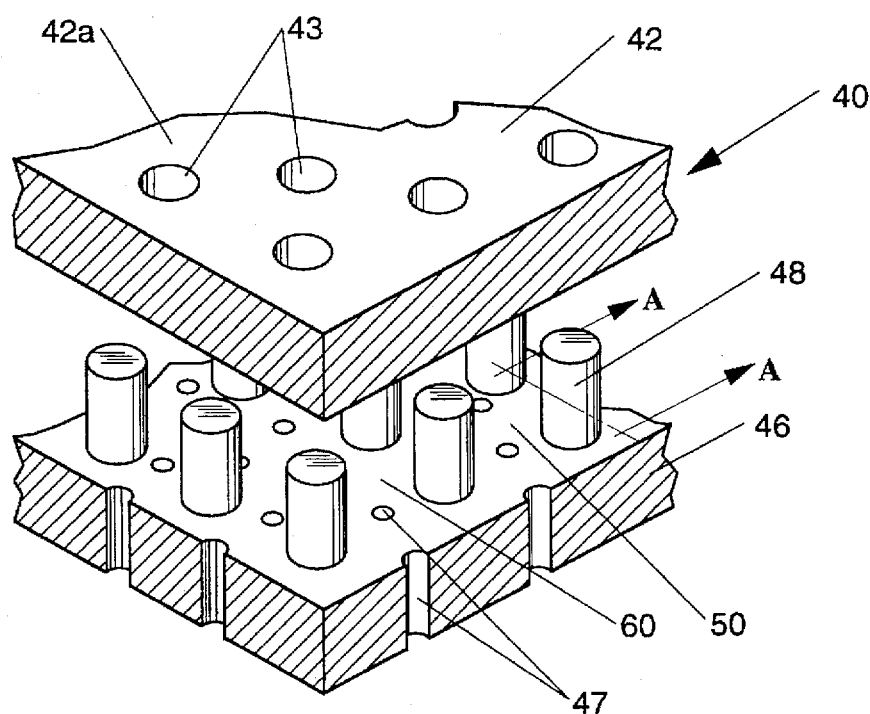
FIG. 1 is a cut-away view of a preferred embodiment of a capillary laminate film.

FIG. 1 depicts a representative capillary laminate material 40 of the type described in the aforementioned Langdon, et al. applications. Capillary laminate material 40 is particularly well suited for use as a topsheet or acquisition layer in a sanitary napkin or other absorbent article. Capillary laminate material 40 shown in FIG. 1 comprises a first fluid pervious sheet or layer 42 and a second fluid pervious sheet or layer 46. The fluid pervious nature of the first sheet 42 and the second sheet 46 is provided by apertures 43 and 47, respectively. While the fluid pervious nature of the first and second sheets 42 and 46 is provided by apertures 43 and 47, it would be obvious to one of ordinary skill in the art that there are other means of imparting a fluid pervious nature to a sheet, such as microporous materials, porous material, slits, etc. The first and second sheets are spaced apart from one another by a spacer. The spacer shown in FIG. 1 comprises a plurality of generally cylindrical spacers 48. Spacers 48 also serve to connect or secure the first sheet 42 to the second sheet 46. Spacers 48 separate first sheet 42 from second sheet 46 such that a "capillary zone" 50 is created between the first sheet 42 and the second sheet 46. As used herein, the term "capillary zone" refers to the space between two adjacent sheets not being occupied by a spacer.

The material selected for the first sheet 42 and the second sheet 46 is preferably machinable and capable of being formed into a sheet. Since the capillary laminate material 40 is to be used in consumer products which contact the human body, the capillary laminate material 40 is preferably soft and safe for epidermal or other human contact. Preferred materials for the first sheet 42 and the second sheet 46 are polymeric materials including, but not limited to polyolefins, particularly polyethylenes, polypropylenes and copolymers having at least one olefinic constituent. Other polymeric materials such as polyester, nylon, copolymers thereof and combinations of any of the foregoing may also be suitable. While first sheet 42 and second sheet 46 are shown as a film, the sheets may, if desired, be in the form of a nonwoven, microporous membrane, foam, etc.

If desired, conventional amounts of agents may also be added to the polymeric matrix of the first sheet 42 and the second sheet 46. It is often desired to add agents to increase the opacity of the sheets. Whiteners, such as titanium dioxide and calcium carbonate may be used to opacity the first and second sheets, 42 and 46, respectively. It may also be desired to add other agents such as surfactants to impart a hydrophilic nature to either the first sheet 42 or the second sheet 46. Degrees and amounts to which agents including whiteners and surfactants are added to the first sheet 42 and the second sheet 46 may be distinct from one another to provide varying effects such as hydrophilicity gradients and the ability to mask fluids within the absorbent article.

The first sheet 42 and the second sheet 46 may themselves be multilayer polymeric films such as those disclosed in commonly assigned U.S. Pat. No. 5,006,394 issued to Baird on Apr. 9, 1991 and U.S. Pat. No. 5,261,899 issued to Visscher et al. on Nov. 16, 1993, said patents being incorporated herein by reference.

The spacers used to form the capillary laminate can be formed from a material which is added to the sheets or from one of the sheets themselves. Examples of materials that can be added include, but are not limited to hot melt adhesives, pressure sensitive adhesives, thermoplastics with a melting point temperature lower than one or more of the sheets, etc. These additional materials can be applied by gravure printing, screen printing or any number of processes which are known to those skilled in the art.

Accordingly, the spacers 48 may be made from any material suitable for securing the first sheet 42 to the second sheet 46. For example, spacers 48 may be made from a heat sealable hot melt adhesive such as Eastobond A3, manufactured by Eastman Chemical, or HL-1412, manufactured by Fuller Adhesive. The spacers 48 may also be made from a polymer material having a lower melting point temperature than the polymeric material used for either the first sheet 42 or the second sheet 46.

The spacers 48 are preferably applied to one of the sheets using a known technique such as gravure printing, screen printing, or transfer printing. When using a pressure sensitive adhesive sufficient pressure must be applied to achieve bonding or securement between the spacers and the respective sheets. When using a hot melt adhesive or a polymeric material having a lower melting point temperature than the materials used for either the first sheet or the second sheet, sufficient heat must be applied to heat the spacers to achieve bonding between the respective sheets.

Alternatively, the spacers 48 may be formed from one or more of the sheets themselves. This can be achieved by embossing, either hot or cold, casting or other processes known to those skilled in the art. The other sheet is then combined with the embossed or cast sheet to form the laminate material of the present invention.

When used as a topsheet on an absorbent article, such as a topsheet on a sanitary napkin, the first sheet 42 becomes the wearer-contacting or body surface of the topsheet. The second sheet 46 becomes the garment facing or pad-contacting surface of the topsheet. Accordingly, as fluid impinges capillary laminate material 40 it first contacts the wearer-contacting surface 42a of the first sheet 42. Fluid then proceeds through apertures 43 and into the capillary zone 50. Upon reaching capillary zone 50 fluid then moves within the capillary zone 50 under capillary pressure. The fluid moves throughout the capillary zone 50 in both the lateral and transverse directions. Simultaneously, the fluid passes through apertures 47 in second sheet 42 and into the acquisition layer of a sanitary napkin.

The dimensions of apertures 43 and 47 in first sheet 42 and second sheet 46, respectively, may be substantially identical to one another or may be of different dimensions. For example, successively smaller apertures in adjacent sheets can be used to create a capillary driving force through the capillary laminate material in the direction of the smaller apertures. When used as a topsheet or an acquisition layer, it may be desirable to have apertures 43 slightly larger than apertures 47 to provide a capillary gradient within capillary laminate material 40. It may also be desirable to vary the dimension of the apertures 43 and 47 within their respective sheets. For example, when used as a topsheet it may be desirable to have the apertures 43 in first sheet 42 which are located in the central region of the sanitary napkin, i.e., the region surrounding the intersection of the longitudinal and transverse centerlines, larger than the apertures adjacent the periphery of the sanitary napkin. The difference in dimension may be easily defined from one region to the next, or may be indiscernible as the dimensions may change gradually from one region to the next region.

In addition to varying the size of apertures 43 and 47 it is also possible to vary the frequency of apertures 43 and 47. For example, when used as a topsheet it may be desirable to have a relatively high frequency of apertures near the central region as compared to the regions near the periphery of the absorbent article. In general, the fewer the apertures and the smaller the apertures the larger the capillary zone defined by the two sheets and the spacers.

The dimension of the capillary zone 50 may be also be varied for particular uses. For example, if used as a topsheet on a disposable diaper, the dimension of capillary zone 50 may be smaller than if used as a topsheet on a sanitary napkin, due to the viscosity and density differences of urine and menses and/or blood. Therefore, the capillary zone for a diaper topsheet will more than likely be smaller than the capillary zone of a sanitary napkin topsheet.

The spacer elements used to both separate and secure the sheets of the capillary laminate material together can be a single spacer or a plurality of spacers having various geometric shapes. The height of the spacers will determine the gap between the sheets or the capillary zone. The capillary zone can be designed to optimally handle different fluids. For example, it has been determined that for blood or menses, the capillary zone should be less than about 0.006 inches (6 mils), more preferably about 0.003 inches (3 mils). Water or urine is best transferred by a smaller capillary zone. The capillary zone may be varied throughout the capillary laminate material. Variability of the capillary zone can be used to encourage fluid flow in the direction of decreasing capillary zone.

The frequency, cross-sectional area, and height of spacers 48 determine to a substantial degree the dimension of the capillary zone 50. The cross-sectional area of the spacers 48 is determined by taking the cross-sectional area of the spacers in a plane substantially parallel to the first and second sheets 42 and 46, respectively, as is indicated by sectional lines A—A in FIG. 1. Spacers 48 are shown as having a circular cross-sectional shape, however, other cross-sectional shapes such as squares, rectangles, ovals, triangles, arcs, dog bone, etc. may also be used for spacers 48.

The sidewalls 49 of spacers 48 are shown as being substantially straight along their length in FIG. 1. However, sidewalls 49 may be concave or convex or any other shape such as sloped, curvilinear, etc. as may be desired.

The spacers may also be used to divide the capillary zone into capillary channels. Capillary channels can be utilized to direct flow within the capillary zone. The capillary channels can be linear, curvilinear or a combination of both. The capillary channels can be uniform in cross-sectional area or they can vary along their length. For example, a decreasing cross-sectional area of a capillary channel can promote fluid flow in the direction of decreasing cross-sectional area.

Within capillary zone 50 there is at least one and more preferably a multiplicity of capillary channels, generally designated as 60. Referring to FIG. 1, as fluid moves between adjacent spacers 48 the shape of the capillary channel 60 between spacers 48 continually changes. Accordingly, the capillary channels 60 have a non uniform shape along their length.

The capillary channels within the capillary zone may take on any shape as desired. For example, the capillary channels may be straight along their entire length, straight along only a portion of their length, continuous along their entire length, discontinuous along their entire length, curvilinear, extend in a fan-like array, oval, hourglass, dog bone, asymmetric, etc.

Figure 2:
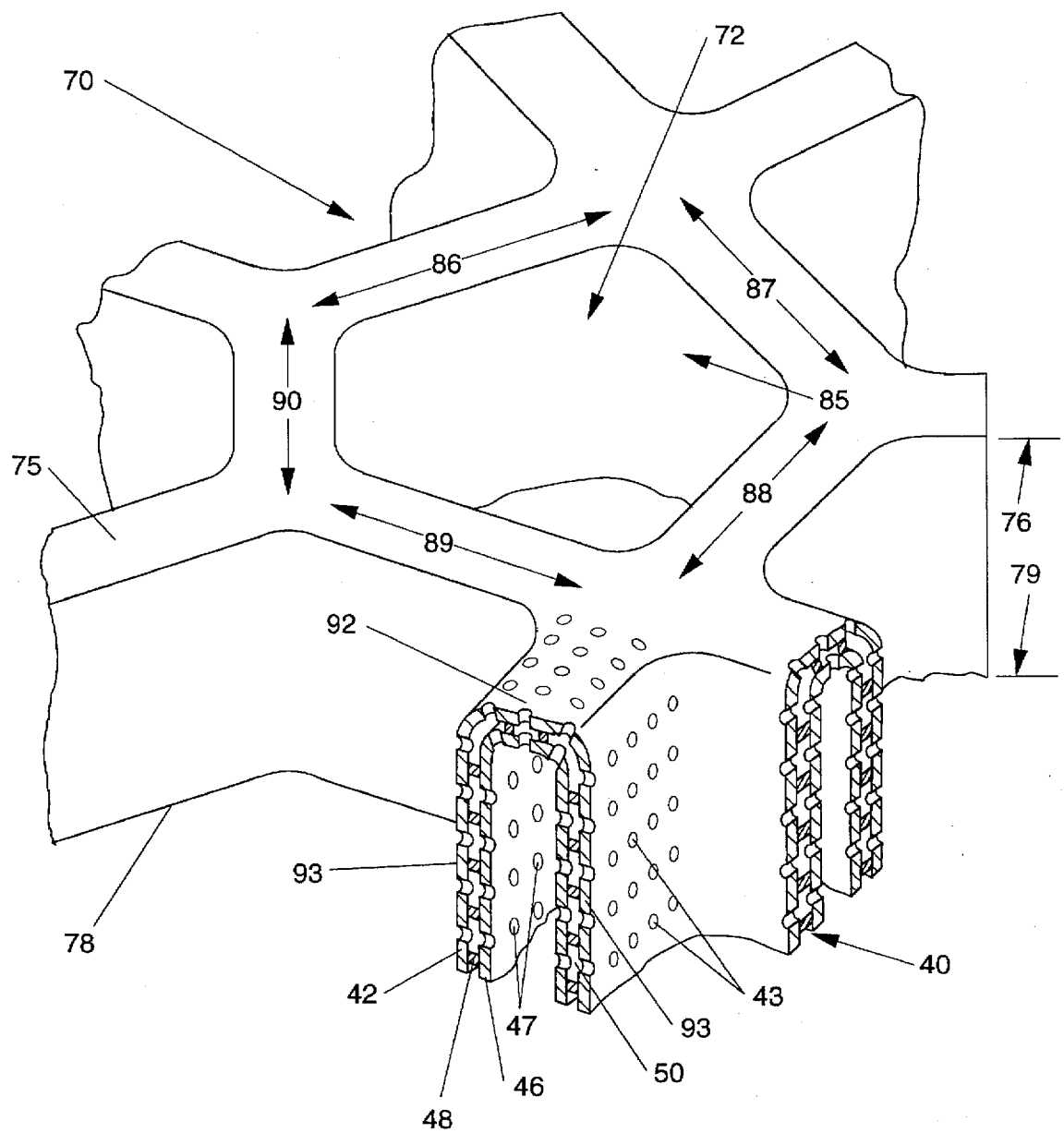
FIG. 2 is an enlarged, partially segmented, perspective illustration of a preferred embodiment of the capillary laminate film of FIG. 1, which has been formed into a macroscopically-expanded, three-dimensional laminate material by the methods of the present invention.

FIG. 2 is an enlarged, partially segmented, perspective illustration of another preferred embodiment of the capillary laminate film of FIG. 1, which has been formed into a macroscopically expanded, three-dimensional, fiber-like, apertured web 70. The overall form/shape of the macroscopically expanded web 70 is generally in accordance with the teachings of commonly assigned U.S. Pat. No. 4,342,314, issued to Radel et al. on Aug. 3, 1982 and hereby incorporated herein by reference. Web 70 has been found suitable for use as a topsheet on a sanitary napkin. The term "macroscopically expanded", when used to describe three-dimensional webs of the present invention, refers to webs, ribbons, and films which have been caused to conform to the surface of a three-dimensional forming structure so that both surfaces thereof exhibit a three-dimensional pattern of surface aberrations corresponding to the macroscopic cross-section of said forming structure. The surface aberrations comprising said pattern being individually discernible to the normal naked eye, i.e., a normal naked eye having 20/20 vision unaided by any instrument that changes the apparent size or distance of an object or otherwise alters the visual powers of the eye, when the perpendicular distance between the viewer's eye and the plane of the web is about 12 inches. The term "fiber-like" as utilized herein to describe the appearance of webs of the present invention, refers generally to any fine-scale pattern of apertures, random or non-random, reticulated or non-reticulated, which connotes an overall appearance and impression of a woven or non-woven fibrous web when viewed by the human eye.

As can be seen in FIG. 2, the webs fiber-like appearance is comprised of a continuum of fiber-like elements, the opposed ends of each of the fiber-like elements are interconnected to at least one other of the fiber-like elements. In the embodiment disclosed in FIG. 2, the interconnected fiber-like elements form a pattern network of pentagonally shaped capillaries 72. The web 70, which exhibits a fiber-like appearance, embodies a three-dimensional microstructure extending from the web's uppermost or wearer-contacting surface 75 in plane 76 to its lowermost or absorbent pad-contacting surface 78 in plane 79 to promote rapid fluid transport from the uppermost surface 75 to the lowermost surface 78 of the web without lateral transmission of fluid between adjacent capillaries 72. As utilized herein, the term "microstructure" refers to a structure of such fine scale that its precise detail is readily perceived by the human eye only upon magnification by a microscope or other means well-known in the art.

Apertures 85 are formed by a multiplicity of intersecting fiber-like elements, e.g., elements 86, 87, 88, 89 and 90, interconnected to one another in the first surface of the web. Each fiber-like element comprises a base portion, e.g., base portion 92, located in plane 76. Each base portion has a sidewall portion, e.g., sidewall portions 93, attached to each edge thereof. The sidewall portions 93 extend generally in the direction of the second surface 78 of the web. The intersecting sidewall portions of the fiber-like elements are interconnected to one another intermediate the first and the second surfaces of the web and terminate substantially concurrently with one another in the plane 79 of the second surface.

In a particularly preferred embodiment, the interconnected sidewall portions terminate substantially concurrently with one another in the plane of the second surface to form apertures in the second surface 78 of the web. The network of capillaries 72 formed by the interconnected sidewall portions allows for free transfer of fluid from the first surface of the web directly to the second surface of the web without lateral transmission of the fluid between the adjacent capillaries.

In addition, small amounts of fluid are able to penetrate the apertures 43 in the first layer 42 of the capillary laminate material 40. The first layer 42 is separated from and secured to the second layer 46 by spacers 48 to provide a capillary zone 50 between the first and second sheets. After penetrating apertures 43, fluid will then move through the capillary zone 50 toward the second surface of the web. Upon reaching the second surface of the web, fluid will be removed from the capillary zone 50 and transmitted to the underlying layer. Fluid may also enter apertures 47 in the second layer 46.

Figure 3:
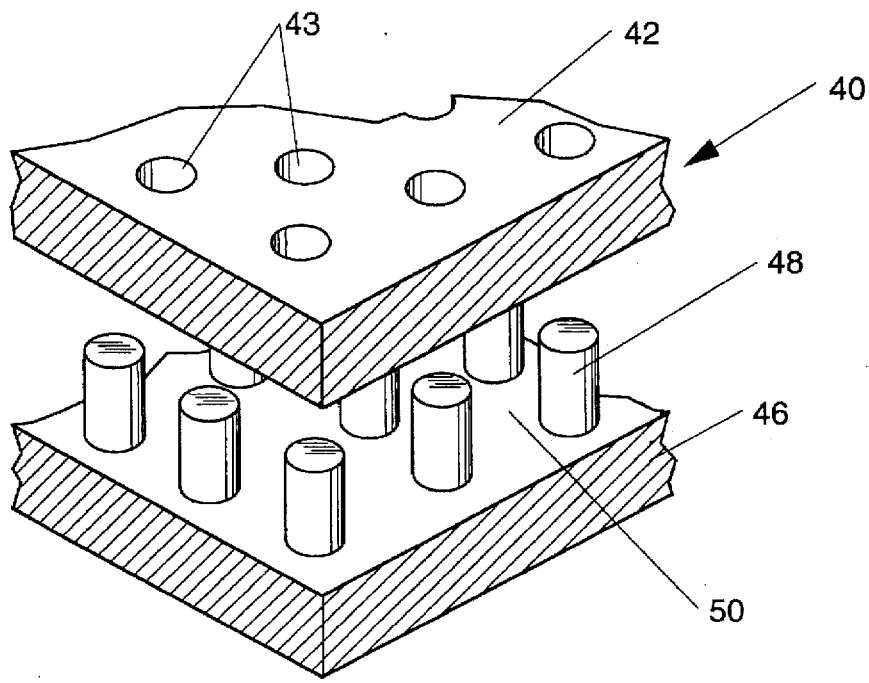
FIG. 3 is a cross-sectional view of another preferred embodiment of a capillary laminate film.

In FIG. 3 there is shown another preferred embodiment of a capillary laminate material 40 of the present invention.

Capillary laminate material 40 comprises a first sheet 42 and a second sheet 46 secured together and spaced apart by a plurality of spacers 48. First sheet 42 includes a plurality of apertures 343. The second sheet 346 is substantially non-apertured, thus preventing fluids from transmitting therethrough. Capillary laminate material 40 may be particularly useful as a macroscopically expanded topsheet such as that shown in FIG. 2 where it is not desired or necessary to have fluid penetrate the second sheet 46. Alternatively, the capillary laminate material 40 may also be used as an absorbent core wherein the second sheet 46 is impervious to liquids and therefore may aid the backsheet in the protection against soiling of undergarments and clothing.

Methods of Making Capillary Laminate Materials.

Figure 4:
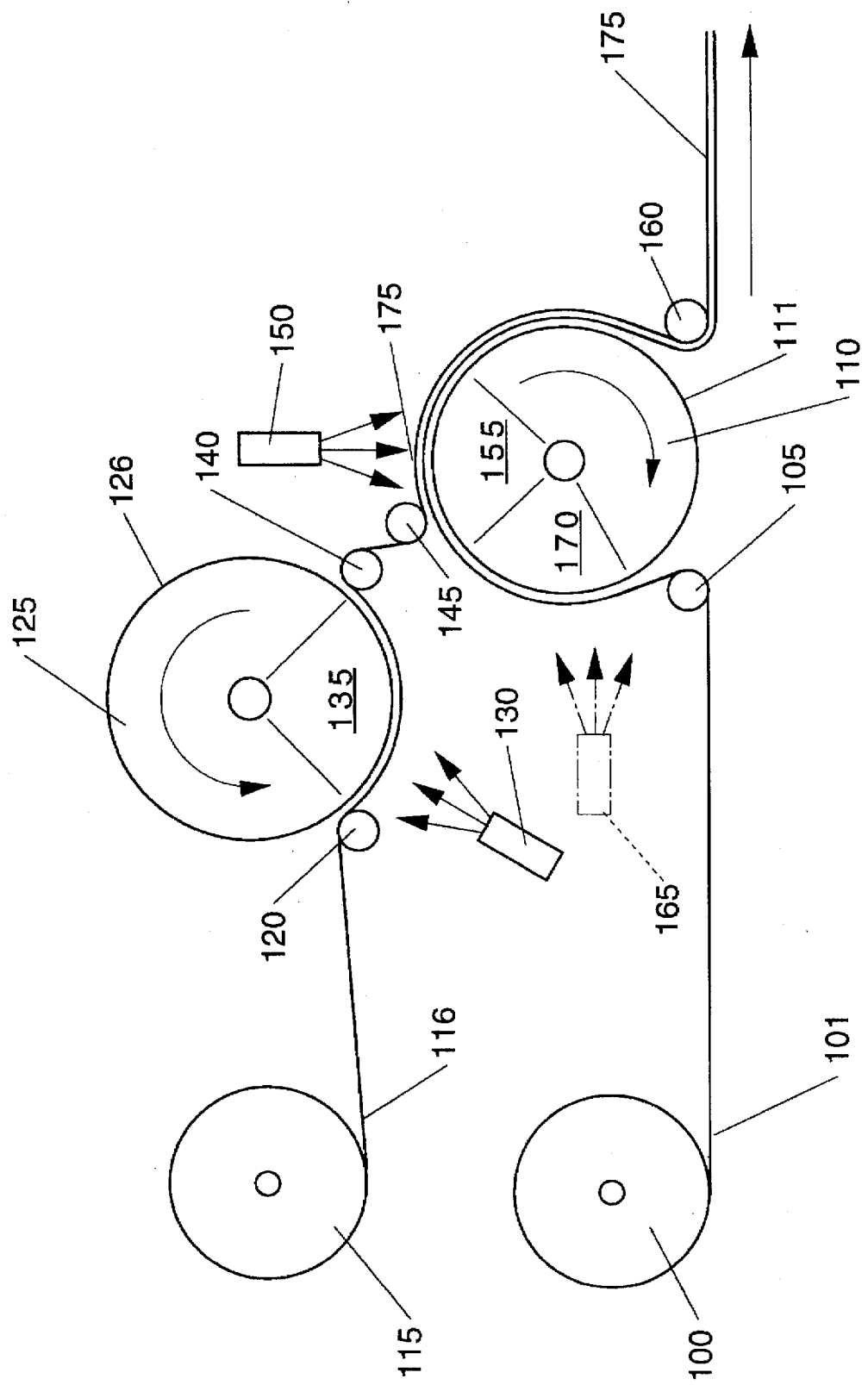
FIG. 4 is a simplified schematic illustration of a preferred process according to the present invention for forming capillary laminate materials.

FIG. 4 is a simplified, schematic flow diagram of a process according to the present invention for producing capillary laminate materials, in particular, three-dimensional, macroscopically expanded capillary laminate materials. A web of substantially planar film 101 comprised of a polymeric material such as polyethylene is fed from supply roll 100 around idler roll 105 and onto the surface of forming drum 110 about which a forming structure 111 continuously rotates at substantially the same speed as the incoming web. The web of film is driven by the forming drum 110. The web 101 contains at least one spacer, and preferably contains a plurality of spacers, on the side facing away from forming drum 110 and is of the general configuration of sheet 46 as discussed above with regard to FIG. 3.

Forming structure 111 comprises a macroapertured surface, such as a patterned network of pentagonally-shaped capillaries, and is preferably constructed generally in accordance with the teachings of U.S. Pat. No. 4,342,314, issued to Radel and Thompson on Aug. 3, 1982, the disclosure of which is hereby incorporated herein by reference. Forming structure 111 is comprised of a plurality of individual photoetched lamina. The apertures in forming structure 111 may be of any desired shape or cross-section when the forming structure is fabricated using the laminar construction techniques generally disclosed in the aforementioned patent.

A second web of substantially planar film 116 comprised of a polymeric material such as polyethylene is fed from supply roll 115 around idler roll 120 and onto the surface of forming drum 125 about which a forming structure 126 continuously rotates at substantially the same speed as the incoming web. The web of film is driven by the forming drum 125.

Forming structure 126 comprises a microapertured surface, such as a woven wire support member, which rotates about a stationary vacuum chamber 135, generally in accordance with the teachings of U.S. Pat. Nos. 4,629,643 and 4,609,518, the disclosures of which are hereby incorporated herein by reference. A high pressure liquid jet nozzle 130 is directed at the surface of the web 116 intermediate a pair of baffles (not shown) as the web traverses the vacuum chamber 135. The high pressure, i.e., preferably at least about 800 psig., jet of liquid causes the web 116 to assume the general contour of the knuckle pattern of the woven wire support member 126. In addition, because the interstices formed by the intersecting filaments are unsupported, the fluid jet causes rupture at those portions of web 116 coinciding with the interstices in the woven wire support structure 126, thereby producing a "microapertured" web. This microapertured web exhibits a multiplicity of fine scale surface aberrations with microapertures coinciding with the point of maximum amplitude of the surface aberrations. The structure and formation of such microapertured webs is described in greater detail in the above-referenced and incorporated U.S. Patents.

After the microaperturing process is completed, the microapertured web is removed from forming structure 126 about an idler roll 140, passed about an idler roll 145, and applied to the outwardly-facing surface (containing the spacers) of the web 101 which was previously applied to the forming structure 111. Alternatively, the forming structures 110 and 125 may be positioned in closer proximity to one another, such that the idler rolls 140 and 145 may be omitted. The microapertured web, when produced by the above-described method, is preferably oriented such that the microscopic surface aberrations are oriented so as to face outwardly away from the forming structure 111.

The forming drum 110 preferably includes an internally located vacuum chamber 155 which is preferably stationary relative to the moving forming structure 111. A pair of stationary baffles (not shown) approximately coinciding with the beginning and end of the vacuum chamber 155 are located adjacent the exterior surface of the forming structure. Intermediate the stationary baffles there is preferably provided means for applying a fluid pressure differential to the laminate web 175 as it passes over the vacuum chamber. In the illustrated embodiment, the fluid pressure differential applicator means comprises a high-pressure liquid nozzle 150 which discharges a jet of liquid, such as water, substantially uniformly across the entire width of web 101. Examples of methods for the production of formed materials using a high-pressure liquid stream are disclosed in U.S. Pat. Nos. 4,695,422, issued to Curro et al. on Sep. 22, 1987; 4,778,644, issued to Curro et al. on Oct. 18, 1988; and 4,839,216, issued to Curro et al. on Jun. 13, 1989, the disclosures of all of these patents being hereby incorporated herein by reference.

The water jet causes the web 101 to conform to the forming structure 111 and apertures the web 101 in the areas coinciding with the capillaries in forming structure 111. In some situations, it may be preferable to heat the liquid stream to cause thermal bonding between the spacers and the second web 116 to form the laminate web 175. The pressure of the liquid stream is preferably selected so as to achieve sufficient conformity of the web to the forming structure without collapsing the capillary zone between the webs or sheets, or compromising the integrity of the sheets themselves.

As an alternative embodiment, it may be desirable to provide an additional high-pressure liquid nozzle 165 and vacuum chamber 170 analogous to nozzle 150 and chamber 155, respectively, to cause the incoming web 101 to conform to the surface of the forming structure 111 before the second incoming web 116 is applied. Such an arrangement may improve the processability and quality of the finished laminate material by pre-forming the first web and reducing the force required to form the laminate as a whole.

Following application of the fluid pressure differential to the web, the three-dimensional, macroscopically-expanded, apertured laminate web 175 is removed from the surface of the forming structure 111 about an idler roll 160 in the condition shown in FIG. 2. The apertured laminate web 175 may be utilized without further processing as a topsheet in an absorbent article. Alternatively, the apertured laminate web 175 may be subjected to further processing, such as ring rolling, creping, or surface treatment as may be desired.

The resulting laminate web 175 exhibits the general overall configuration of FIG. 2, with the upper sheet being fluid pervious and the lower sheet being fluid-impervious, as depicted in FIG. 3. If a laminate web with both sheets being fluid pervious is desired, such as depicted in FIG. 1, the lower sheet may be apertured prior to lamination by the method disclosed above with regard to the upper sheet, or by any other suitable method, so as to assume the configuration of sheet 46 of FIG. 1.

Figure 5:
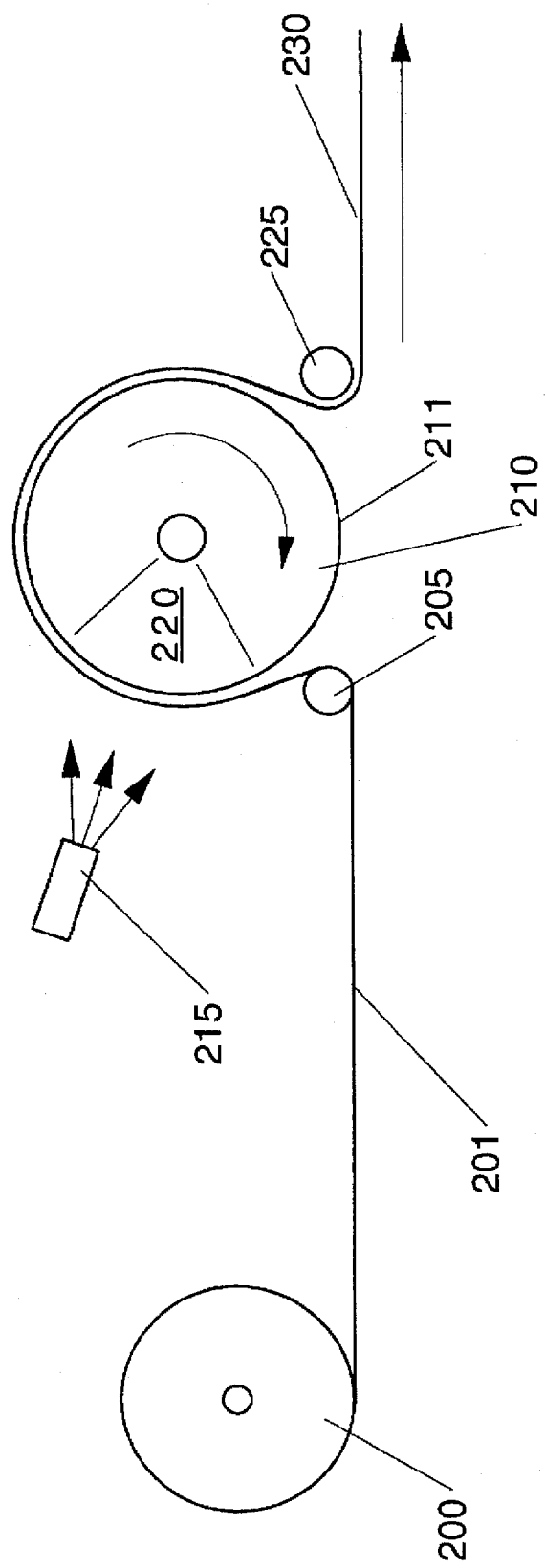
FIG. 5 is a simplified schematic illustration of another preferred process according to the present invention for forming capillary laminate materials.

FIG. 5 is a simplified schematic diagram of another preferred process according to the present invention for producing capillary laminate webs. A co-wound web of substantially planar film comprised of a polymeric material such as polyethylene, spacer element or elements, and microapertured planar film comprised of a polymeric material such as polyethylene, is fed from supply roll 200 around idler roll 205 and onto the surface of forming drum 210 about which a forming structure 211 continuously rotates at substantially the same speed as the incoming web. It may be desirable to pre-bond the first and second webs or sheets to one another before or during the pre-winding of the supply roll 200. The web of film is driven by the forming drum 210. The web 201 is oriented such that the microapertured web faces away from the forming structure 211, and is of the general configuration of sheet 46 as discussed above with regard to FIG. 3. The microapertured web may be produced by the method described above with regard to FIG. 4 or any other suitable method, and if produced as described above is preferably oriented with the microscopic surface aberrations facing away from the other film components and away from forming structure 211.

Forming structure 211 is generally similar to the forming structure 111 shown in FIG. 4, and comprises a macroapertured surface, such as a patterned network of pentagonally-shaped capillaries. As before, the apertures in forming structure 211 may be of any desired shape or cross-section when the forming structure is fabricated using the laminar construction techniques generally disclosed with regard to FIG. 4.

The forming drum 210 preferably includes an internally located vacuum chamber 220 which is preferably stationary relative to the moving forming structure 211. The structure and operation of the forming drum 210 is substantially as described above with regard to forming drum 110 depicted in FIG. 4. In the illustrated embodiment, the fluid pressure differential applicator means comprises a high-pressure liquid nozzle 215 which discharges a jet of liquid, such as water, substantially uniformly across the entire width of web 201.

The water jet causes the web 201 to conform to the forming structure 211 and apertures the laminate web 230 in the areas coinciding with the capillaries in forming structure 211. In some situations, it may be preferable to heat the liquid stream to cause thermal bonding between the spacers and the second web to form the laminate web 230. The pressure of the liquid stream is preferably selected so as to achieve sufficient conformity of the web to the forming structure without collapsing the capillary zone between the webs or sheets, or compromising the integrity of the sheets themselves.

Following application of the fluid pressure differential to the web, the three-dimensional, macroscopically-expanded, apertured laminate web 230 is removed from the surface of the forming structure 211 about an idler roll 225. The apertured laminate web 230 may be utilized without further processing as a topsheet in an absorbent article. Alternatively, the apertured laminate web 230 may be subjected to further processing, such as ring rolling, creping, or surface treatment as may be desired.

The resulting laminate web 230 exhibits the general overall configuration of FIG. 2, with the upper sheet being fluid pervious and the lower sheet being fluid-impervious, as depicted in FIG. 3. If a laminate web with both sheets being fluid pervious is desired, such as depicted in FIG. 1, the lower sheet may be apertured prior to lamination by the method disclosed above with regard to the upper sheet, or by any other suitable method, so as to assume the configuration of sheet 46 of FIG. 1.

Figure 6:
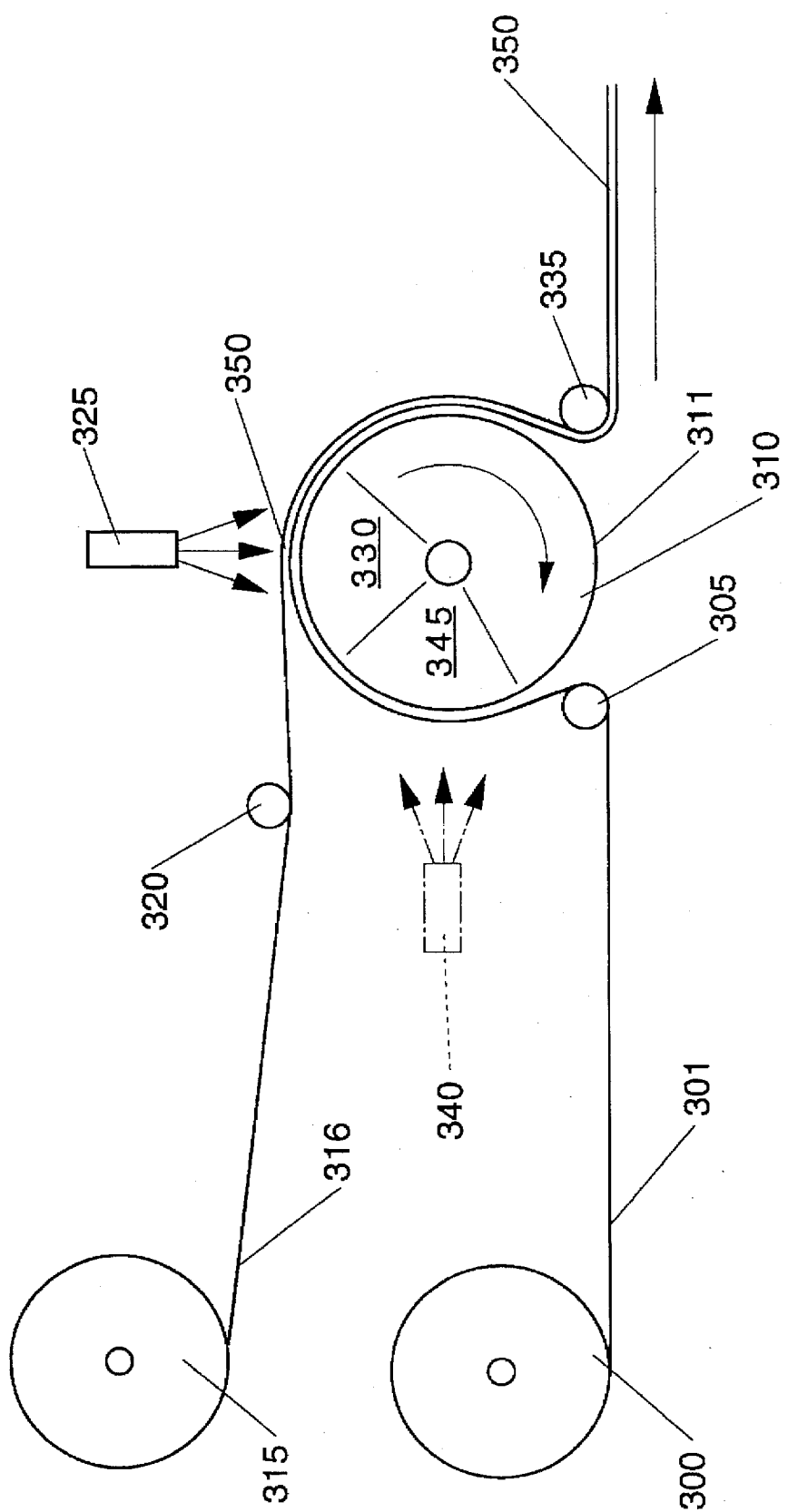
FIG. 6 is a simplified schematic illustration of another preferred process according to the present invention for forming capillary laminate materials.

FIG. 6 is a simplified schematic diagram of another preferred process according to the present invention for producing capillary laminate webs. A web of substantially planar film comprised of a polymeric material such as polyethylene is fed from supply roll 300 around idler roll 305 and onto the surface of forming drum 310 about which a forming structure 311 continuously rotates at substantially the same speed as the incoming web. The web of film is driven by the forming drum 310. The web 301 contains at least one spacer, and preferably contains a plurality of spacers, on the side facing away from forming drum 310 and is of the general configuration of sheet 46 as discussed above with regard to FIG. 3.

A second microapertured web of substantially planar film 316 comprised of a polymeric material such as polyethylene is fed from supply roll 315 around idler roll 320 and onto the surface of forming drum 310. The microapertured web may be produced by the method described above with regard to FIG. 4 or any other suitable method, and if produced as described above is preferably oriented with the microscopic surface aberrations facing away from the other film components and away from forming structure 311.

Forming structure 311 is generally similar to the forming structure 111 shown in FIG. 4, and comprises a macroapertured surface, such as a patterned network of pentagonally-shaped capillaries. As before, the apertures in forming structure 311 may be of any desired shape or cross-section when the forming structure is fabricated using the laminar construction techniques generally disclosed with regard to FIG. 4.

The forming drum 310 preferably includes an internally located vacuum chamber 320 which is preferably stationary relative to the moving forming structure 311. The structure and operation of the forming drum 310 is substantially as described above with regard to forming drum 110 depicted in FIG. 4. In the illustrated embodiment, the fluid pressure differential applicator means comprises a high-pressure liquid nozzle 315 which discharges a jet of liquid, such as water, substantially uniformly across the entire width of web 350.

The water jet causes the webs 301 and 316 to conform to the forming structure 311 and apertures the laminate web 350 in the areas coinciding with the capillaries in forming structure 311. In some situations, it may be preferable to heat the liquid stream to cause thermal bonding between the spacers and the second web to form the laminate web 350. The pressure of the liquid stream is preferably selected so as to achieve sufficient conformity of the web to the forming structure without collapsing the capillary zone between the webs or sheets, or compromising the integrity of the sheets themselves.

As an alternative embodiment, it may be desirable to provide an additional high-pressure liquid nozzle 340 and vacuum chamber 345 analogous to nozzle 325 and chamber 330, respectively, to cause the incoming web 301 to conform to the surface of the forming structure 311 before the second incoming web 316 is applied. Such an arrangement may improve the processability and quality of the finished laminate material by pre-forming the first web and reducing the force required to form the laminate as a whole.

Following application of the fluid pressure differential to the web, the three-dimensional, macroscopically-expanded, apertured laminate web 350 is removed from the surface of the forming structure 311 about an idler roll 335. The apertured laminate web 350 may be utilized without further processing as a topsheet in an absorbent article. Alternatively, the apertured laminate web 350 may be subjected to further processing, such as ring rolling, creping, or surface treatment as may be desired.

The resulting laminate web 350 exhibits the general overall configuration of FIG. 2, with the upper sheet being fluid pervious and the lower sheet being fluid-impervious, as depicted in FIG. 3. If a laminate web with both sheets being fluid pervious is desired, such as depicted in FIG. 1, the lower sheet may be apertured prior to lamination by the method disclosed above with regard to the upper sheet, or by any other suitable method, so as to assume the configuration of sheet 46 of FIG. 1.

Although in the foregoing illustrative process descriptions spacers have been initially provided on the outwardly-facing surface of the web closest to the forming structure, it may be desirable under some circumstances to form or provide the spacers on the inwardly-facing side of the web farthest from the forming structure. It may also be desirable to provide spacers on both webs on their facing surfaces.

In addition, the processes described herein may be adapted and expanded to produce capillary laminate materials having more than two sheets of material, in particular 3 or more sheets with a plurality of spacers between adjacent sheets, to form capillary laminate materials of the types generally described in the aforementioned Langdon et al. U.S. Patent Applications.

While particular embodiments of the present invention have been illustrated and described, it would be obvious to one skilled in the art that there is other changes and modifications that can be made without departing from the spirit and scope of the present invention. It is therefore intended to cover in the appended claims all such changes and modifications that are within the scope of this invention.

What is claimed is:

1. A process for forming a three-dimensional, macroscopically-expanded capillary laminate web, said web being comprised of a first sheet of polymeric material and a second sheet of polymeric material, said second sheet having a first surface and a second surface, said first sheet being fluid pervious, said first sheet and said second sheet being spaced apart from one another by at least one one spacer to define a capillary zone therebetween for the capillary movement of fluid, said process comprising the steps of:
    (a) feeding said first and second sheets onto a first forming structure having opposed surfaces such that said second surface of said second sheet is in contact with said first forming structure and said first sheet is in contact with said first surface of said second sheet, at least one of said sheets having said spacer on a surface thereof between said first and second sheets, said first forming structure exhibiting a multiplicity of apertures which place the opposed surfaces of said first forming structure in fluid communication with one another; and
    (b) applying a fluid pressure differential across the thickness of said first and second sheets, said fluid pressure differential being sufficiently great to cause said first and second sheets to rupture in those areas coinciding with said apertures in said first forming structure and to conform with said first forming structure.

2. The process of claim 1, wherein said web includes a plurality of spacers.

3. The process of claim 2, further comprising the step of applying said spacers onto said first surface of said second sheet prior to feeding said second sheet onto said first forming structure.

4. The process of claim 1, wherein said second sheet is fed onto said first forming structure before said first sheet is fed onto said first forming structure.

5. The process of claim 4, further comprising the step of applying a fluid pressure differential across the thickness of said second sheet prior to the step of feeding said first sheet onto said first forming structure, said fluid pressure differential being sufficiently great to cause said second sheet to rupture in those areas coinciding with said apertures in said first forming structure and to conform with said first forming structure.

6. The process of claim 1, further comprising the step of rendering said first sheet fluid pervious prior to feeding said first sheet onto said first forming structure.

7. The process of claim 1, wherein said second sheet is fluid pervious.

8. The process of claim 1, wherein said fluid pressure differential comprises a heated high pressure jet of liquid.

9. The process of claim 2, wherein said spacers comprise a hot melt adhesive.

10. The process of claim 1, wherein said web comprises more than two sheets and a plurality of spacers between adjacent sheets.

11. A process for forming a three-dimensional, macroscopically-expanded capillary laminate web, said web being comprised of a first sheet of polymeric material and a second sheet of polymeric material, said second sheet having a first surface and a second surface, said first sheet being fluid pervious, said first sheet and said second sheet being spaced apart from one another by a plurality of spacers to define a capillary zone therebetween for the capillary movement of fluid, said process comprising the steps of:
    a) feeding said second sheet onto a first forming structure having opposed surfaces such that said second surface of said second sheet is in contact with said forming structure, said first forming structure exhibiting a multiplicity of apertures which place the opposed surfaces of said first forming structure in fluid communication with one another;
    (b) feeding said first sheet onto a second forming structure having opposed surfaces, said second forming structure exhibiting a multiplicity of apertures which place the opposed surfaces of said second forming structure in fluid communication with one another, said first sheet being initially fluid impervious;
    (c) applying a fluid pressure differential across the thickness of said first sheet, said fluid pressure differential being sufficiently great to cause said first sheet to rupture in those areas coinciding with said apertures in said second forming structure and to conform with said second forming structure, thereby rendering said first sheet fluid pervious;
    (d) feeding said first sheet onto said first surface of said second sheet, at least one of said sheets having said spacers on a surface thereof between said first and second sheets; and
    (e) applying a fluid pressure differential across the thickness of said first and second sheets, said fluid pressure differential being sufficiently great to cause said first and second sheets to rupture in those areas coinciding with said apertures in said first forming structure and to conform with said first forming structure.

12. The process of claim 11, further comprising the step of applying said spacers onto said first surface of said second sheet prior to feeding said second sheet onto said first forming structure.

13. The process of claim 11, further comprising the step of applying a fluid pressure differential across the thickness of said second sheet prior to the step of feeding said first sheet onto said first forming structure, said fluid pressure differential being sufficiently great to cause said second sheet to rupture in those areas coinciding with said apertures in said first forming structure and to conform with said first forming structure.

14. A process for forming a three-dimensional, macroscopically-expanded capillary laminate web, said web being comprised of a first sheet of polymeric material and a second sheet of polymeric material, said second sheet having a first surface and a second surface, said first sheet being fluid pervious, said first sheet and said second sheet being spaced apart from one another by a plurality of spacers to define a capillary zone therebetween for the capillary movement of fluid, said process comprising the steps of:
  (a) assembling said first and second sheets in overlying relation to one another, at least one of said sheets having said spacers on a surface thereof between said first and second sheets;
  (b) feeding said first and second sheets onto a first forming structure having opposed surfaces such that said second surface of said second sheet is in contact with said first forming structure and said first sheet is in contact with said first surface of said second sheet, said first forming structure exhibiting a multiplicity of apertures which place the opposed surfaces of said first forming structure in fluid communication with one another; and
  (c) applying a fluid pressure differential across the thickness of said first and second sheets, said fluid pressure differential being sufficiently great to cause said first and second sheets to rupture in those areas coinciding with said apertures in said first forming structure and to conform with said first forming structure.

15. The process of claim 14, further comprising the step of applying said spacers onto said first surface of said second sheet prior to assembling said first and second sheets.

16. The process of claim 14, further comprising the step of bonding said first and second sheets together after said first and second sheets are assembled and before feeding said first and second sheets onto said first forming structure.

17. A process for forming a three-dimensional, macroscopically-expanded capillary laminate web, said web being comprised of a first sheet of polymeric material and a second sheet of polymeric material, said second sheet having a first surface and a second surface, said first sheet being fluid pervious, said first sheet and said second sheet being spaced apart from one another by a plurality of spacers to define a capillary zone therebetween for the capillary movement of fluid, said process comprising the steps of:
  (a) feeding said second sheet onto a first forming structure having opposed surfaces such that said second surface of said second sheet is in contact with said first forming structure, said first forming structure exhibiting a multiplicity of apertures which place the opposed surfaces of said first forming structure in fluid communication with one another;
  (b) feeding said first sheet onto said first surface of said second sheet, at least one of said sheets having said plurality of spacers on a surface thereof between said first and second sheets; and
  (c) applying a fluid pressure differential across the thickness of said first and second sheets, said fluid pressure differential being sufficiently great to cause said first and second sheets to rupture in those areas coinciding with said apertures in said first forming structure and to conform with said first forming structure.

18. The process of claim 17, further comprising the step of applying said spacers onto said first surface of said second sheet prior to feeding said second sheet onto said first forming structure.

19. The process of claim 17, further comprising the step of applying a fluid pressure differential across the thickness of said second sheet prior to the step of feeding said first sheet onto said first forming structure, said fluid pressure differential being sufficiently great to cause said second sheet to rupture in those areas coinciding with said apertures in said first forming structure and to conform with said first forming structure.

20. The process of claim 17, further comprising the step of rendering said first sheet fluid pervious prior to feeding said first sheet onto said first forming structure.

* * * * *